United States Patent [19]

Rein

[11] Patent Number: 4,462,265

[45] Date of Patent: Jul. 31, 1984

[54] MULTIPLE DEPTH WATER SAMPLING SYSTEM

[75] Inventor: Charles R. Rein, Panama City Beach, Fla.

[73] Assignee: The United States of America as represented by the Secretary of the Navy, Washington, D.C.

[21] Appl. No.: 470,119

[22] Filed: Feb. 28, 1983

[51] Int. Cl.³ .............................................. G01N 1/16
[52] U.S. Cl. ............................. 73/863.33; 73/170 A; 73/863.72; 73/864.34
[58] Field of Search ........... 73/170 A, 863.31, 863.33, 73/863.71, 863.72, 863.73, 864.31, 864.33, 864.34, 864.35, 864.51, 864.62, 864.63, 864.64

[56] References Cited

U.S. PATENT DOCUMENTS

| | | | |
|---|---|---|---|
| 2,846,121 | 8/1958 | Ronnebeck | 73/863.72 |
| 3,159,173 | 12/1964 | Fremon | 73/863.72 X |
| 3,176,517 | 4/1965 | Chelminski . | |
| 3,314,009 | 4/1967 | Murdock . | |
| 3,339,417 | 7/1967 | Richard . | |
| 3,513,709 | 5/1970 | Pullos | 73/170 AX |
| 3,537,316 | 11/1970 | Stewart et al. | 73/170 A |
| 3,751,983 | 8/1973 | Rutkowski et al. | 73/864.35 |
| 3,803,919 | 4/1974 | Tarsing | 73/864.35 |
| 3,841,156 | 10/1974 | Wolfe | 73/864.31 X |
| 3,848,464 | 11/1974 | Scheipner et al. | 73/170 A |
| 3,927,562 | 12/1975 | Hickey, Jr. | 73/170 A |
| 4,019,380 | 4/1977 | Raymond | 73/170 A |
| 4,100,805 | 7/1978 | Cossin | 73/864.63 X |

FOREIGN PATENT DOCUMENTS 783629  11/1980  U.S.S.R. ............................ 73/863.31

OTHER PUBLICATIONS

"A Six-Port Underway Water Sampling System"; MTS Journal, vol. 15, No. 1; 5-1981; pp. 26-30; Marshall H. Orr et al.

Primary Examiner—Jerry W. Myracle
Assistant Examiner—Tom Noland
Attorney, Agent, or Firm—Robert F. Beers; Harvey A. David

[57] ABSTRACT

A towed system for collecting water samples from a plurality of individual depths for serial presentation to analyzing instruments utilizes a plurality of pressure actuated collection devices separated by vertical hose segments through which water is pumped from a depressor. The flow is modulated to actuate collection device valves so as to introduce the samples in stacked relation.

8 Claims, 6 Drawing Figures

MULTIPLE DEPTH WATER SAMPLING SYSTEM

BACKGROUND OF THE INVENTION

This invention relates to the field of ocean water sampling, and more particularly to apparatus for gathering samples from multiple depths for inspection by instrumentation for detecting the presence of matter such as contaminants and relating it to the zone from which the collection was made.

Prior sampling apparatus for that purpose have involved strings of collecting bottles, multiple conduit hose systems, and complex electronic sensor systems requiring considerable underwater electronics. These prior approaches have either been too slow for practical large area surveys, have been subject to inordinate power requirements, or have been complex, costly, and unreliable.

SUMMARY OF THE INVENTION

With the foregoing in mind, it is a principal object of this invention to provide a ship deployed multiple depth water sampling system that can gather samples for inspection by on board instrumentation for detection of water borne contaminants.

Another object is to provide such a system or apparatus that is simple and reliable in operation, can travel at substantial forward speeds, and operate with a minimum of power requirements.

As another object, the invention aims to gather samples from multiple depths, which samples are placed in serial relation available for rapid, sequential, analysis for content, whereby automated recording of the depth and geographic location can readily be accomplished.

Other objects and many of the attendant advantages will be readily appreciated as the subject invention becomes better understood by reference to the following detailed description, when considered in conjunction with the accompanying drawings.

DESCRIPTION OF THE PREFERRED EMBODIMENT

Figure 1:
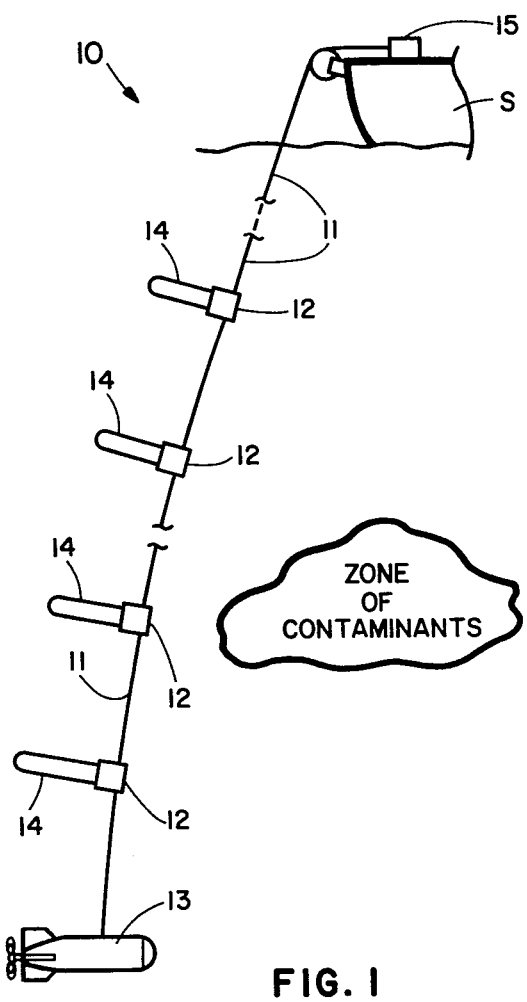
FIG. 1 is a side elevational view illustrating multiple depth sampling apparatus embodying the invention shown in association with a deploying surface vessel.
Figure 6:
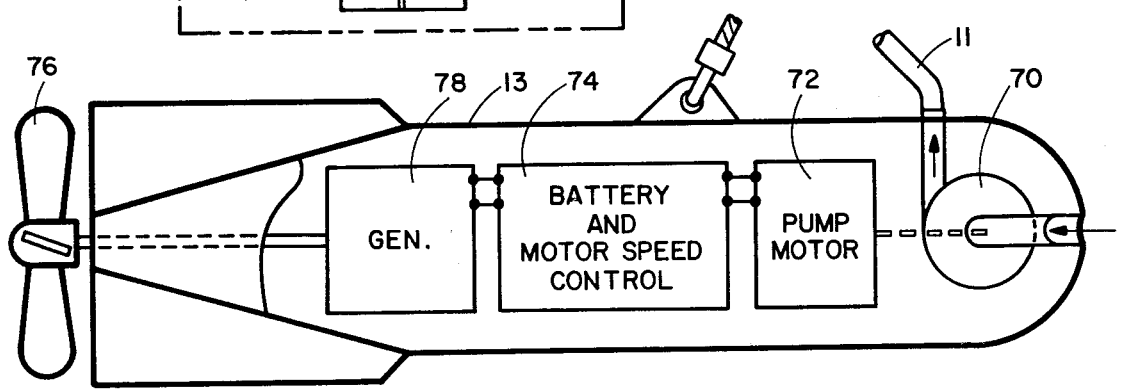
FIG. 6 is a diagrammatic illustration of a depresser and pump device forming part of the apparatus.

Referring to FIG. 1, on exemplary water sampling system 10 is deployed from a surface ship S and comprises segments 11 of faired hose that link a plurality of collection valve devices 12. A depressor 13, later described in more detail with reference in FIG. 6 is located at a lower end of the apparatus and contains a water pump for operation of the system. Each of the collection valve devices 12 is provided with a U-shaped length of tubing 14 which is normally open to the ambient water, and which can be periodically closed by operation of the valve devices 12 so as to entrain a sample in the flow of water from the depressor pump through the line hose segments 11 to the ship S. By appropriate timing of actuation of all of the valves, as will later be described, a series of samples can be obtained. The series of samples are delivered to shipboard instrumentation for analysis of content, or to some other designated utilization means.

Figure 2:
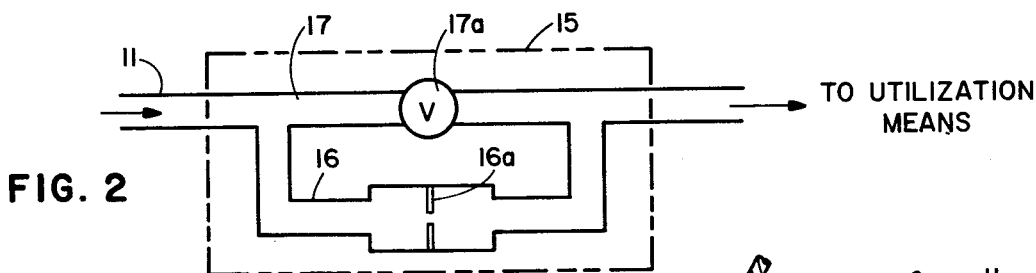
FIG. 2 is a schematic illustration of pressure modulator portion of the system.

In the embodiment being described, the valve devices 12 are adapted to be actuated by changes in pressure in the water flowing upwardly through the hose segments 11 and through the valve devices. Referring to FIG. 2, the uppermost hose segment 11 is connected to a pressure modulator 15 comprising parallel flow paths 16 and 17. The path 16 imposes a flow restriction 16a, while path 17 includes a flow interrupting valve 17a. The latter is operable between fully closed and fully open positions. When the valve 17a is open, the water in collection system moves under the influence of the depresser pump and the pressure is relatively low. When the valve 17a is closed, all of the water must flow through the striction 16a and the pressure throughout the system is elevated.

Figure 3:
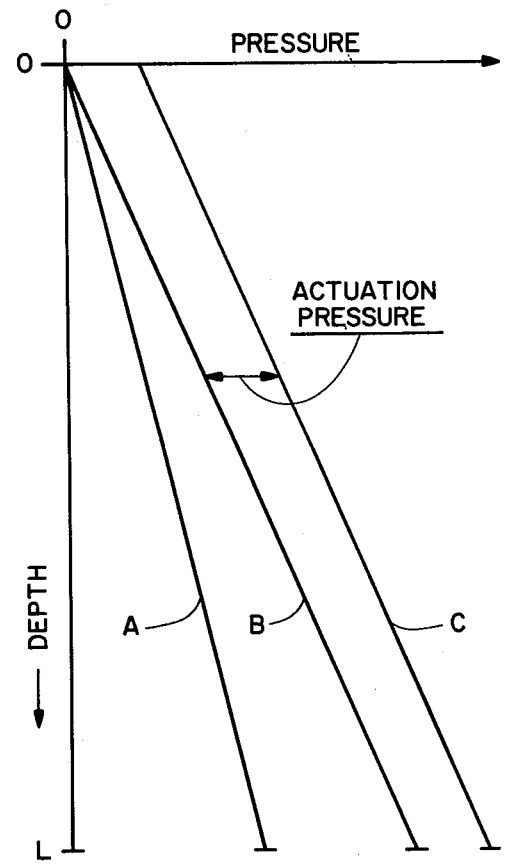
FIG. 3 is a graphic illustration showing certain pressure relationships of the apparatus.

The graph in FIG. 3 shows the pressure to the hose vs. depth. The curve A is the hydrostatic head which increases linearly with depth. The difference between curves A and B represents the difference between internal and external pressure along the hose caused by the frictional loss in the hose. This difference decreases linearly with distance along the hose from the pump to the outlet. Therefore, when the outlet valve 17a is open, curve B represents the internal pressure vs. position on the hose. However, when the outlet valve is closed, the pressure everywhere in the hose increases by an amount equal to the actuation pressure. In that case, the pressure vs. position in the hose is represented by curve C.

Figure 4:
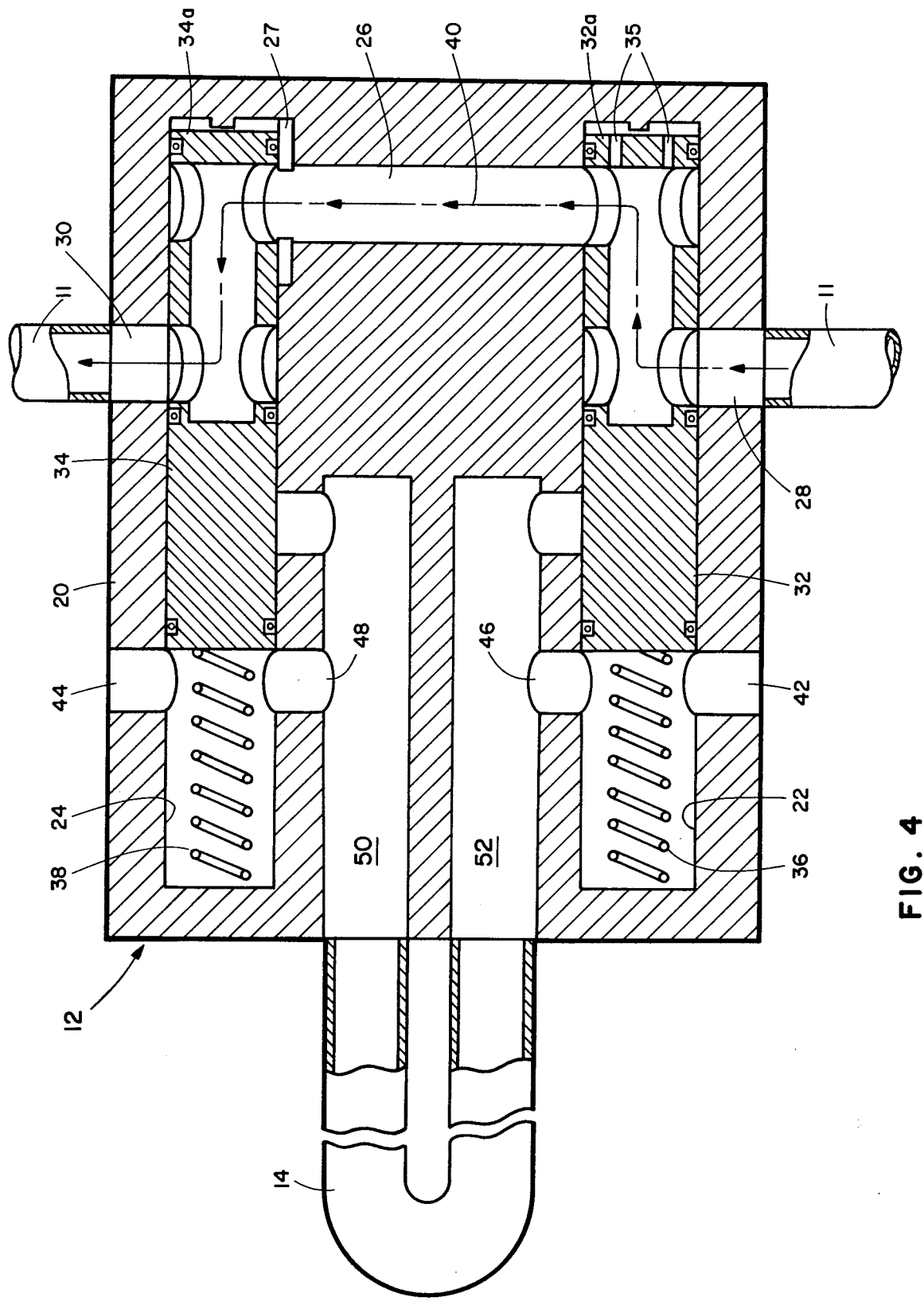
FIG. 4 is an enlarged sectional view of a sampling valve device of one of the multiple sampling stations of the apparatus of FIG. 1.

Referring now to FIG. 4, the valve 12 comprises a body 20 having two cylindrical bores 22,24 interconnected near one end of each of the bores by a passage 26. The block is relieved to form a groove 27 in the bore 24 and intersecting with the upper end of the passage 26. An inlet port 28, communicating with the bore 22, is connected to a segment of the hose 11 to receive water being pumped up the hose from depressor 13. An outlet port 30, communicating with the bore 24, is connected to an upper segment of the hose 11.

Reciprocably disposed in the bores 22,24 are first and second shuttles 32 and 34 each having a hollow, ported portion and a solid portion. The shuttles are normally held in the positions of FIG. 4 by springs 36, 38 so that the hollow, ported portions permit water flow from the lower segment of hose 11, through inlet port 28, shuttle 32, passage 26, shuttle 34, and outlet port 30 to the upper segment of hose 11, as indicated by flow arrows 40. It will be noted that the end wall 32a of shuttle 32 is provided with apertures 35.

The block 20 further has sample inlet ports 42,44 communicating through bores 22,24 and ports 46,48 to passages 50, and 52, respectively. The passages 50,52 are connected to opposite ends of the sample collecting U-tube 14. With the shuttles 32,34 positioned as in FIG. 4, the ports 42,44 are open to ambient water and allow filling of the U-tube 14.

Figure 5:
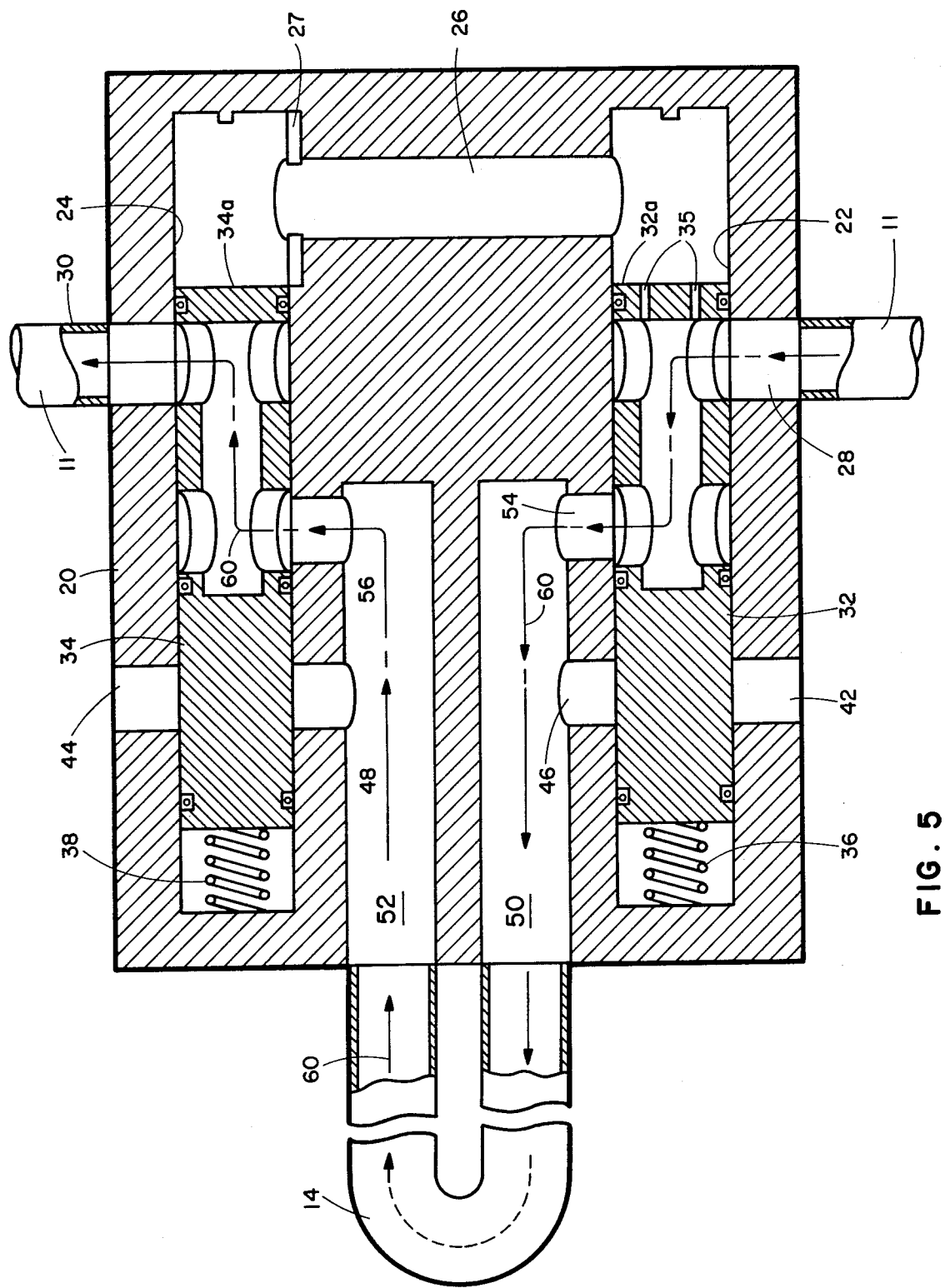
FIG. 5 is a view similar to FIG. 4 but showing parts in different operating positions.

Upon a predetermined increase in pressure in hose 11, effected by the valve and restriction at the upper end of the system, the shuttles 32,34 are moved to the positions illustrated in FIG. 5. In that view, the solid portions of the shuttles block ports 42,44,46, and 48 and divert water from the lower segment of hose 11, through the shuttle 32, a port 54, passage 50, tube 14, passage 52, a port 56, shuttle 34, and port 30 to the upper segment of hose 11, as indicated by flow arrows 60. When the hose pressure is cycled in its lower value, the shuttles return to the positions of FIG. 4. The groove 27 and apertures 35 prevent the shuttles 32,34 from becoming locked in either of their operative positions. It will be recognized that each actuation of the valve 12 will introduce a water sample into the system.

The system 10 allows collection of water samples from multiple depths at high speed with minimum complexity. Because it is impractical to attempt to pump all samples to the surface between valve actuations, except at very low speeds or large horizontal sampling spacings, the system can be operated to "stack" the relatively short lengths (five feet) of sample water in the hose. The invention contemplates collection of samples at the nine depths which correspond to the depressor plus eight inlet valves spaced, say, fifty feet apart along the hose. The upper inlet valve can be at any desired shallow depth. The other may be at progressively greater depths to the maximum which can be provided by the depressor. For a forward speed of ten knots, the valve actuation period would be approximately three seconds to gather samples every fifty feet of forward travel. The "stack" the samples in the hose the velocity of the samples with respect to the hose must be 45.3 ft/sec this corresponds to a volume flow rate of 1.9 ft$^3$/min or 14.3 gal/min and require a valve actuation time of $\frac{1}{3}$ sec for each three second cycle.

Referring now to FIG. 6, the depressor 13 must provide a substantial downward force to give the system a large vertical aperture and it houses the pump 70, a pump motor 72 and a battery and speed control section 74. A turbine 76 and generator 78 are conveniently provided to maintain the battery from which the pump draws electrical power. This configuration allows use of the tow hose not only as a conduit of water samples to the surface and a communications link to the inlet valves but also as a mechanical power link to the depressor. The extra ships thrust that is required to pull the turbine through the water is then the source of power to charge the batteries and run the pump water. The advantages of this configuration include deletion of all electrical apparatus in the water except within the confines of the depressor and also potential use of modified hydraulic hose as the tow hose instead of a costly special hybrid electrical conductor-and-tube tow cable.

From the foregoing, it will be appreciated that a string of novel sampling valves actuated by the pressure in the hose conducting the samples is advantageously simple compared to prior systems. The use of a depressor including turbine means for generating pump activating power avoids the need if a combined water conduit and electric power cable. Stacking of the samples by timed, synchronized sampling permits rapid, coverage of a swept zone with good detection resolution.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. Apparatus for collecting water samples from a plurality of depths, said apparatus comprising:
   hose means adapted to be towed substantially vertically through a body of water;
   depressor means at the lower end of said hose means for keeping that end at a predetermined depth;
   pump means, carried by said depressor means for pumping water from said predetermined depth through said hose means to a surface station;
   modulator means at said surface station for periodically limiting flow of water at the upper end of said hose means so as to produce periodic pressure pulses in said water in said hose means along its entire length; and
   a plurality of collection devices, each located at a predetermined individual depth of interest in spaced relation along said hose means, said collection devices being responsive to said pressure pulses to introduce water samples from the respective depths of interest into said hose means for transit to said surface station.

2. Apparatus as defined in claim 1, and wherein each of said collection devices comprises:
   a collection chamber normally open to the ambient water at the corresponding depth of interest so as to accumulate water therefrom;
   collection valve means responsive to said pressure pulses to place said chamber in series with segments of said hose means above and below the respective collection device, whereby water previously collected in said chamber is introduced into said hose means as a sample.

3. Apparatus as defined in claim 2, and wherein:
   said collection valve means comprises a valve body having a plurality of bores intercommunicating with one another, with said hose means segments and with said chamber; and
   a plurality of spool valve members each reciprocable in a separate one of said bores between first and second positions for selectively controlling flow between said hose means segments and between said segments and said chamber.

4. Apparatus as defined in claim 3, and wherein:
   said collection chamber comprises U-shaped length of tubing extending from said valve body.

5. Apparatus as defined in claim 4, and wherein said modulator means comprises:
   valve means connected between the upper end of said hose means and utilization means and operable to periodically change the restriction to flow from said hose means.

6. Apparatus as defined in claim 4, and wherein said collection valve means further comprises:
   spring means normally urging said spool valve members into said first positions; and
   said spool members being movable to said second positions by said pressure pulses.

7. Apparatus as defined in claim 6, and wherein:
   said modulator is operative to produce said pulses to be of predetermined frequency and duration, whereby samples from said individual depths of interest are stacked therefrom serially in said hose means for delivery sequentially to utilization means at said surface station.

8. Apparatus as defined in claim 2, and wherein said modulator means comprises:
   means defining first and second parallel flow passages at the upper end of said hose means;
   a first, substantially fixed flow restrictor in one of said flow passages;
   a second, variable flow restrictor in the other of said flow passages; and
   means for causing said second flow restrictor to vary flow in said other flow passage.

* * * * *